(12) United States Patent
Mukhopadhyay et al.

(10) Patent No.: US 8,383,867 B2
(45) Date of Patent: Feb. 26, 2013

(54) METHOD FOR PRODUCING FLUORINATED ORGANIC COMPOUNDS

(75) Inventors: Sudip Mukhopadhyay, Williamsville, NY (US); Haridasan K. Nair, Williamsville, NY (US); Rajesh K. Dubey, Williamsville, NY (US); Rajiv R. Singh, Getzville, NY (US); George A. Shia, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 943 days.

(21) Appl. No.: 11/592,476

(22) Filed: Nov. 3, 2006

(65) Prior Publication Data

US 2007/0112229 A1 May 17, 2007

Related U.S. Application Data

(63) Continuation-in-part of application No. 11/118,504, filed on Apr. 29, 2005, now Pat. No. 7,371,904, and a continuation-in-part of application No. 11/118,503, filed on Apr. 29, 2005, now Pat. No. 7,345,209, and a continuation-in-part of application No. 11/118,530, filed on Apr. 29, 2005, now Pat. No. 7,189,884.

(60) Provisional application No. 60/567,426, filed on Apr. 29, 2004, provisional application No. 60/567,429, filed on Apr. 29, 2004, provisional application No. 60/567,427, filed on Apr. 29, 2004, provisional application No. 60/567,425, filed on Apr. 29, 2004, provisional application No. 60/567,428, filed on Apr. 29, 2004, provisional application No. 60/733,378, filed on Nov. 3, 2005.

(51) Int. Cl.
*C07C 17/25* (2006.01)
*C07C 19/08* (2006.01)
*C07C 21/18* (2006.01)
*C07C 17/00* (2006.01)
*C07C 23/00* (2006.01)
*C07C 25/13* (2006.01)
*C07C 22/00* (2006.01)

(52) U.S. Cl. ........ 570/155; 570/123; 570/124; 570/140; 570/144; 570/156; 570/153; 570/159

(58) Field of Classification Search .................. None
See application file for complete search history.

(56) References Cited

U.S. PATENT DOCUMENTS

| | | | |
|---|---|---|---|
| 2,931,840 A | 4/1960 | Marquis .................... 260/653.3 | |
| 2,996,555 A | 8/1961 | Rausch et al. | |
| 3,472,826 A | 10/1969 | Potts et al. | |
| 3,505,417 A | 4/1970 | Gardner | |
| 3,659,023 A | 4/1972 | Regan | |
| 4,086,407 A | 4/1978 | Fozzard .......................... 526/75 | |
| 4,650,914 A | 3/1987 | Woodard et al. | |
| 4,798,818 A | 1/1989 | Baizer et al. | |
| 4,900,874 A | 2/1990 | Ihara et al. | |
| 5,162,594 A | 11/1992 | Krespan | |
| 5,532,419 A | 7/1996 | Van Der Puy et al. | |
| 5,545,777 A | 8/1996 | Morikawa et al. | |
| 5,574,192 A | 11/1996 | Van Der Puy et al. | |
| 5,608,126 A * | 3/1997 | Morikawa et al. ............ 570/167 | |
| 5,679,875 A | 10/1997 | Aoyama et al. | |
| 5,710,382 A | 1/1998 | Dunmead et al. | |
| 5,986,151 A | 11/1999 | Van Der Puy | |
| 6,023,004 A | 2/2000 | Thenappan et al. | |
| 6,031,141 A | 2/2000 | Mallikarjuna et al. | |
| 6,066,769 A | 5/2000 | Nappa et al. | |
| 6,111,150 A | 8/2000 | Sakyu et al. | |
| 6,124,510 A * | 9/2000 | Elsheikh et al. .............. 570/156 | |
| 6,369,284 B1 | 4/2002 | Nappa et al. | |
| 6,548,719 B1 * | 4/2003 | Nair et al. ..................... 570/157 | |
| 6,809,226 B1 | 10/2004 | Pennetreau et al. | |
| 6,958,424 B1 | 10/2005 | Nair et al. | |
| 6,977,316 B1 | 12/2005 | Mukhopadhyay et al. | |
| 7,026,520 B1 | 4/2006 | Mukhopadhyay et al. | |
| 7,026,521 B1 | 4/2006 | Mukhopadhyay et al. | |
| 7,071,367 B1 | 7/2006 | Mukhopadhyay et al. | |
| 7,132,578 B1 | 11/2006 | Mukhopadhyay et al. | |
| 7,135,601 B2 * | 11/2006 | Mukhopadhyay et al. ... 570/226 | |
| 7,189,884 B2 | 3/2007 | Mukhopadhyay et al. | |
| 7,196,236 B2 | 3/2007 | Mukhopadhyay et al. | |
| 7,371,904 B2 * | 5/2008 | Ma et al. ........................ 570/136 | |
| 2003/0060670 A1 | 3/2003 | Nair et al. ..................... 570/155 | |
| 2005/0020862 A1 | 1/2005 | Tung et al. | |
| 2005/0080302 A1 | 4/2005 | Baker et al. | |
| 2005/0090698 A1 | 4/2005 | Merkel et al. | |
| 2005/0171391 A1 | 8/2005 | Janssens et al. | |
| 2005/0245774 A1 * | 11/2005 | Mukhopadhyay et al. ... 570/171 | |
| 2006/0217577 A1 | 9/2006 | Mukhopadhyay | |
| 2006/0258891 A1 | 11/2006 | Mukhopadhyay et al. | |

(Continued)

FOREIGN PATENT DOCUMENTS

EP     522639     1/1993
EP    0522639     1/1993

(Continued)

OTHER PUBLICATIONS

JP-04-110388 patent (Derwent abstract) "Fluid for Heat Transfer" published Apr. 10, 1992.*

(Continued)

*Primary Examiner* — Johann Richter
*Assistant Examiner* — Clinton Brooks
(74) *Attorney, Agent, or Firm* — Bruce O. Bradford

(57) ABSTRACT

Disclosed is a method for producing fluorinated organic compounds, including hydrofluoropropenes, which preferably comprises converting at least one compound of formula (I):

$$CF_3CF_nCH_mX_{a-m} \quad\quad\quad (I)$$

to at least one compound of formula (II)

$$CF_3CZCHZ \quad\quad\quad (II).$$

where each X is independently Cl, F, I or Br; each Z is independently H or F; n is 1 or 2; m is 1, 2 or 3, provided that when n is 1, m is 1 or 2; a is 2 or 3, and a-m≧0. Certain embodiments include the step of reacting fluorinated C2 olefin, such as tetrafluoroethylene, with a Cl addition agent under conditions effective to produce a compound of formula (I).

24 Claims, No Drawings

U.S. PATENT DOCUMENTS

| | | | |
|---|---|---|---|
| 2007/0112227 A1 | 5/2007 | Mukhopadhyay et al. | |
| 2007/0112228 A1 | 5/2007 | Mukhopadhyay et al. | |
| 2007/0112230 A1 | 5/2007 | Mukhopadhyay et al. | |
| 2007/0129580 A1 | 6/2007 | Mukhopadhyay et al. | |

FOREIGN PATENT DOCUMENTS

| | | | |
|---|---|---|---|
| EP | 0644173 | | 3/1995 |
| EP | 974571 | A2 | 1/2000 |
| GB | 844597 | | 8/1960 |
| GB | 1171202 | | 11/1969 |
| JP | 0411038 | A * | 5/1992 |
| JP | 11140002 | | 5/1999 |
| JP | 2000169404 | | 6/2000 |
| JP | 2000178543 | | 6/2000 |
| WO | 9008752 | | 8/1990 |
| WO | WO9008748 | | 8/1990 |
| WO | WO 9504021 | | 2/1995 |
| WO | WO/96/01797 | A | 1/1996 |
| WO | WO98/42645 | | 3/1998 |
| WO | WO 98/21171 | | 5/1998 |
| WO | 99/48993 | | 9/1999 |
| WO | 00/39242 | | 7/2000 |
| WO | WO 01/07384 | | 2/2001 |
| WO | 03027051 | | 4/2003 |
| WO | 2005/012212 | | 2/2005 |
| WO | WO2005/042451 | A | 5/2005 |
| WO | 2005108332 | | 11/2005 |
| WO | 2005108334 | | 11/2005 |
| WO | 2007019355 | A | 2/2007 |

OTHER PUBLICATIONS

Hazeldine, R N et al; "Addition of Free Radicals to Unsaturated Systems. XIII. Direction of Radical Addition to Chloro-1, 1-Difluoroethylene"; Journal of the Chemical Society; 1957; pp. 2193-2197; XP009081235.

McDoniel, J Bridget et al; "Thresholdenergy and Unimolecular Rate Constant for Elimination of HF from Chemically Activated CF3CF2CH3; Effect of the CF3 Substituent on the .Alpha.-Carbon"; Journal of Physical Chemistry A; 1997; pp. 1334-1337; XP002426456.

Belen'kii G G et al; "Electrophilic, Catalyticalkylation of Polyfluoroolefins by some Fluoroalkenes"; Journal of Fluorine Chemistry, Elsevier, NL; 2001; pp. 15-20; XP004231215.

Paleta, O et al; "Synthesis of Perfluoroallyl Chloride and Some Chlorofluorophopenes"; Bulletin de la Societe Chimique de France, Societe Francaise de Chimie, Paris, France; 1986; pp. 920-924; XP009088473.

Tamuma, T et al; "19F Nuclear Magnetic Resonance Studies of Halogenated Propanes"; Journal of Fluorine Chemistry, Elsevier, NL; pp. 259-284; XP002546058.

Paleta, O et al; "Addition Reactions of Haloolegins. XI. Reaction of Tetrafluoroethylene with Monofluoromethanes in the presence of Aluminum Chloride"; Collection of Czechoslovak Chemical Communications; 1971; pp. 1867-1875; XP009071825.

Posta A et al; "Raecton of Trifluoroethylene with Fluorochloromethanes in the Presence of Aluminum Chloride"; Collection of Czechoslovak Chemical Communications; 1974; pp. 1330-1335; XP009148472.

Paleta, O et al; "Addition Reactions of Haloolefins. X. The Reactivity of Monfluorochloromethanes and Influence of Solvents on the Addition Rate of Halogenomethanes"; Collection of Czechoslovak Chemical Communications; 1971; pp. 2062-2066; XP009148480.

Banks, et al., Journal of Fluorine Chemistry, vol. 82, Issue 2, pp. 171-174 (1997).

Database Beilstein, Beilstein Institute for Organic Chemistry, M. Van Der Puy: J. Fluorine Chemistry, vol. 81, No. 2, 1997, pp. 187-192 XP002424669.

Database Beilstein, Beilstein Institute for Organic Chemistry, Haszeldine, Steele: J. Chem. Soc. 1953, p. 1592, 1597, XP0022424670.

Database WPI Week 199812, AN 1998-126110, XP002427152, Derwent Publications Ltd., London, GB & JP 10 007605A (Central Glass Co Ltd) Jan. 13, 1998 abstract.

Database Beilstein, XP002426121, 1952, 2504-2506.

Gambareto et al., "The Reaction of chlorine monofloride with unsaturated compounds", 1976, XP00246119.

Henne, Albert L., et al., Chlorinated Derivatives of 2-Floropropane[1] J. American Chemical Society, Jul. 11, 1941: pp. 2692-2694, vol. 63.

J Burdon et al.: J. Fluorine Chemistry, vol. 40, pp. 283-318, XP002424668, 1988

Knunyants, I. L. et al. Reaction of Fluoro Olefins, Institute of Heteroorganic Compounds, Bulletin of the Academy of Sciences of USSR, Division of Chemical Sciences—ISSN 0568-5230, p. 1312-1317, 1959.

Kunshenko B V et al.: Reaction of Organic Compounds with SF4-HF-Hallogenating System VII, 1992, XP002344564.

March, J. Advanced Organic Chemistry, 1997, pp. 631-636, McGraw-Hill International Book Company, XP002427150.

U.S. Appl. No. 10/694,273, filed Oct. 27, 2003, Singh et al.

Zhuranl Organieheskoi Khimii, 28(4), 672-80, (1982).

Free-radical additions to unsaturated systems, Journal of Chemical Society, Section C: Organic, (3), 414-21, p. 415, 1970.

Dickson, R.S, Fluorcarbon-Aluminium Compounds, Aust. J. Chem., 1972, 25, 761-8.

Vittorio Montanari, A Novel Synthesis of Perhalogenated Alkenes, J. Org. Chem. 1992, 57, 5018-5019.

* cited by examiner

METHOD FOR PRODUCING FLUORINATED ORGANIC COMPOUNDS

CROSS-REFERENCES TO RELATED APPLICATIONS

This application is claiming the priority benefit of U.S. Provisional Application Ser. No. 60/733,378, filed Nov. 3, 2005, and is Continuation-in-Part of U.S. patent application Ser. No. 11/118,503, filed on Apr. 29, 2005 (now U.S. Pat. No. 7,345,209), which in turn claims the priority benefit of U.S. Provisional Patent Application Nos. 60/567,427 and 60/567,425 filed Apr. 29, 2004.

This application is also a Continuation-in-Part of U.S. patent application Ser. No. 11/118,504, filed on Apr. 29, 2005 (now U.S. Pat. No. 7,371,904), which in turn claims the priority benefit of U.S. Provisional Patent Application Nos. 60/567,426 and 60/567,429 filed Apr. 29, 2004.

This application is also a Continuation-in-Part of U.S. patent application Ser. No. 11/118,530, filed on Apr. 29, 2005 (now U.S. Pat. No. 7,189,884), which in turn claims the priority benefit of U.S. Provisional Patent Application No. 60/567,428, filed Apr. 29,2004.

The disclosures of each of the above-mentioned applications are incorporated herein by reference. Also incorporated herein by reference are the following U.S. Applications identified by Attorney Docket Nos. 60/733,444; 60/733383; 60/733,355; 60/733,377 and 60/733,379, each of which was filed on Nov. 3, 2005.

BACKGROUND OF INVENTION

(1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) (HFO is hydrofluorolefin) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts, including a sizeable amount of carbon black. The carbon black is not only unwanted, it tends to deactivate the catalyst used in the process.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Catalyzed hydrogen reduction reactions have been disclosed for the preparation of fluorinated C3 hydrocarbons in U.S. Pat. No. 5,545,777. The patent describes the reaction as being one in which a compound of formula (1)

$$C_3H_aCl_bF_c \qquad (1)$$

is converted by catalyzed hydrogen reduction to a compound of formula (2)

$$C_3H_{a+x}Cl_{b-y}F_{c-z} \qquad (2)$$

where a, b, c, x, y and z are integers satisfying the following conditions: $a \geq 0$, $b \geq 1$, $c \geq 2$, $x \geq 1$, $y \geq 1$, $z \geq 0$, $a+b+c=8$, $x=y+z$, $b-y \geq 0$, and $c-z \geq 2$. Since the reactions disclosed in this patent require a reaction product in which $a+b+c=8$ and that $x=y+z$, it is not possible for the disclosed reaction product to include C3 olefins, which as mentioned above have been found to be desirable for use in many important applications.

Notwithstanding prior teachings applicants appreciate a continuing need for methods of efficiently preparing certain hydrofluorocarbons, particularly tetrafluorpropenes such as HFO-1234yf.

SUMMARY OF THE INVENTION

Applicants have discovered a method for producing fluorinated organic compounds, including hydrofluoropropenes, which preferably comprises converting at least one compound of formula (I):

$$CF_3CF_nCH_mX_{a-m} \qquad (I)$$

to at least one compound of formula (II)

$$CF_3CZ=CHZ \qquad (II).$$

where each X is independently Cl, I or Br; each Z is independently H or F; n is 1 or 2; m is 1, 2 or 3, provided that when n is 1, m is 1 or 2; a is 2 or 3, and $a-m \geq 0$. In certain preferred embodiments, each Z is different. Formula II is intended to include all possible isomers.

The preferred converting step of the present invention comprises catalytic reduction of the compound of formula (I). The catalytic reduction step comprises in preferred embodiments introducing said compound of formula (I) to a reaction system under conditions effective to convert, and preferably convert at least about 50%, more preferably at least about 70%, and even more preferably at least about 90%, of said compound of formula (I). It is also generally preferred that said converting step produces a reaction product having at least about 20% selectivity, more preferably at least about 40% selectivity and even more preferably at least about 70% selectivity, to compounds of formula (II), preferably tetrafluoropropene, and even more preferably HFO-1234yf.

In certain preferred embodiments, the converting step comprises reacting a compound of formula (I) in the gas phase, in the liquid phase, or a combination of these, with gas phase reactions preferably occurring in the presence of catalyst.

DETAILED DESCRIPTION OF PREFERRED EMBODIMENTS

One beneficial aspect of the present invention is that it enables the production of desirable fluroolefins, preferably C3 fluoroolefins, using relatively high conversion and high selectivity reactions. In addition, the methods of the present invention provided reactions with relatively high yield and which are capable of obtaining relatively long catalyst life.

Furthermore, the present methods in certain preferred embodiments permit the products of the desirable fluorolefins from relatively attractive starting materials. Ethylene and is halogentated derivates, such as tertrafluorethylene, may in certain embodiments be an advantageous starting material because such products are relatively easy to handle, and are generally readily available in commercial quantities and/or can be easily produced from other readily available materials. For example, the compounds of formula (I) can be synthesized by the catalyzed gas phase addition of $CH_2FCl$ and $CF_2=CF_2$.

Thus, in certain embodiments the present methods include the step of reacting fluorinated C2 olefin, such as tetrafluoroethylene, with a Cl addition agent under conditions effective to produce a compound of formula (I)

$$CF_3CF_nCH_mX_{a-m} \quad (I)$$

where X, n, m, and a are indicated above. In preferred embodiments, the fluorinated olefin reactant is a compound of formula (III)

$$CY_2=CY_2 \quad (III)$$

where each Y is independently F, Cl, I or Br, provided that at least one F on each carbon atom, and the Cl addition agent comprises a compound of formula (IV)

$$CH_mY_{a-m} \quad (IV)$$

Where Y is as indicated above and m is 1, 2 or 3; a is 2 or 3, and a-m>0. In preferred embodiments, the compound of formula (III) comprises a compound of formula (IIIA)

$$CF_2=CY_2 \quad (IIIA)$$

where each Y is independently F or Cl, and the compound of formula (IV) comprises a compound of formula (IVA)

$$CH_2FCl \quad (IVA).$$

The reaction by which the compound of formula (III) is converted to a compound of formula (I) is sometimes referred to herein for convenience, but not necessarily by way of limitation, as an addition reaction.

Of course, it is also contemplated that the compounds of formula (I) will, in certain embodiments, themselves be attractive starting materials for the production of the desired fluorinated olefin in accordance with the present invention, and therefore certain embodiments of the present invention do not include the addition reaction described herein.

Preferably the formula (I) compound, which in certain embodiments is preferably formed by a process comprising a catalyzed Cl addition reaction, is then exposed to reaction conditions effective to produce a reaction product containing one or more of the desired fluorolefins, preferably one or more compounds of formula (II). In one preferred aspect of the present invention, the conversion step comprises a reaction that is sometimes referred to herein for convenience, but not necessarily by way of limitation, as a reduction reaction and in other aspects as a fluorination dehydrohalogenation reaction. Preferred aspects of each of the preferred steps is described below, with the titles used as headings for these steps being used for convenience but not necessarily by way of limitation.

I. Addition Reaction

In preferred embodiments, the reactant compound of formula (III) is fluorinated olefin, more preferably fluorinated ethylene and even more preferably $CF_2=CF_2$ (sometimes referred to herein as "TFE") or $CF_2=CFCl$ (sometimes referred to herein as "CTFE"). Preferably, one or more fluorinated ethylene compounds are reacted with one or more of $CH_2FCl$.

In certain preferred embodiments, the addition step comprises contacting, (preferably by introducing into a reactor) the compounds in an $CH_mY_{a-m}$:formula III mole ratio of from about 1:1 to about 200:1, more preferably from about 1:1 to about 100:1 and even more preferably of from about 2:1 to about 3:1. In preferred embodiments in which the compound of $CH_mY_{a-m}$ comprises $CH_2FCl$ and the formula III compound comprises $CF_2=CF_2$, the $CH_2FCl$:TFE mole ratio of the feeds to the reactor are from about 1:1 to about 200:1, more preferably from about 1:1 to about 100:1 and even more preferably from about 1.5:1 to about 2:1.

It is contemplated that this reaction step can be carried out in the liquid phase or in the gas phase, or a combination of liquid/gas phases, and it is further contemplated that the reaction can be carried out batch wise, continuous, or a combination of these.

Thus, it is contemplated that the addition step, when it is used, may be preformed using a wide variety of process parameters and process conditions in view of the overall teachings contained herein. However, it is preferred in certain embodiments that this reaction step comprise a gas phase reaction, preferably in the presence of catalyst, supported on carbon or unsupported, preferably a metal-based catalyst, such as antimony-based catalysts (such as $SbF_3$, $SbF_5$, and partially flourinated $SbCl_3$ or $SbCl_5$) aluminum-based catalyst (such as $AlCl_3$), iron-based catalyst such $FeCl_3$ including such catalysts on a carbon or other appropriate support. It is expected that many other catalysts may be used depending on the requirements of particular embodiments, and of course, two or more any of these catalysts, or other catalysts not named here, may be used in combination.

The gas phase addition reaction may be conducted, for example, by introducing a gaseous form of a compound of formula (III) and formula (IV) into a suitable reaction vessel or reactor. Preferably the vessel is comprised of materials which are resistant to corrosion, such as Hastelloy, Inconel, Monel and/or fluoropolymers linings. Preferably the vessel contains catalyst, for example a fixed or fluid catalyst bed, packed with a suitable addition catalyst, with suitable means to heat the reaction mixture to the desired reaction temperature.

While it is contemplated that a wide variety of reaction temperatures and pressures may be used, depending on relevant factors such as the catalyst being used and the most desired reaction product, it is generally preferred that at least a portion of the addition step is carried out at a reaction temperature of from about 5° C. to about 1000° C., more preferably 5° C. to about 500° C., more preferably 5° C. to about 200° C. and even more preferably from about 40° C. to about 60° C. for reactors which are preferably maintained at a pressure of from about 1 to about 1500 psig, and even more preferably from about 20 to about 40 psig.

In certain preferred embodiments, the compound of formula (III) and the compound of formula (IV) are introduced into an appropriate reaction vessel in the form of a gas and the reactor is preferably maintained at a temperature of about 50° C. and the reactor is preferably maintained at a pressure of about 30 psig.

In preferred embodiments the conversion of the formula (III) compound, particularly formula (IIIA) compound(s), is preferably at least about 15%, more preferably at least about 20%, and selectivity to compounds of formula I is preferably at least about 50%, more preferably at least about 70%, and even more preferably at least about 75%.

II. Formation of the Compound of Formula II

The methods of the present invention preferably comprise converting a compound of formula (I) to a fluorolefin, preferably a C3 fluorolefin, more preferably a compound of formula (II), and even more preferably tetrafluoropropene.

In certain preferred embodiments, the present converting step is carried out under conditions effective to provide a formula (I) conversion of at least about 40%, more preferably at least about 55%, and even more preferably at least about 70%. In certain preferred embodiments the conversion is at least about 90%, and more preferably about 100%. Further in certain preferred embodiments, the conversion of the compound of formula I to produce a compound of formula II is conducted under conditions effective to provide a formula II selectivity of at least about 25%, more preferably at least about 40%, more preferably at least about 70%, and even more preferably at least about 90%.

This reaction step can be carried out in the liquid phase or in the gas phase, or in a combination of gas and liquid phases, and it is contemplated that the reaction can be carried out batch wise, continuous, or a combination of these.

A. Gas Phase Dehydrohalogenation

One preferred reaction step in accordance may be described by those reactions in which the compound of formula (I) comprises a compound in which n is 2, that is a compound of formula (IA)

$$CF_3CF_2CH_mX_{a-m} \quad\quad\quad (IA).$$

For example, one preferred compound of formula (IA) is 1,1,1,2,2-pentafluoro-3chloropropane ($CF_3CF_2CH_2Cl$). By way of illustration but not necessarily by way of limitation, an embodiment involving this compound may be shown to proceed by the following reaction, where the reducing agent is hydrogen:

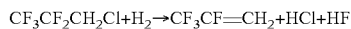

$$CF_3CF_2CH_2Cl+H_2 \rightarrow CF_3CF=CH_2+HCl+HF$$

Although applicant does not intend to be bound to or limited by any particular theory of operation, is believed that in some embodiments the above noted reaction proceeds by the formation of another compound in accordance with formula (IA), namely, $CF_3CF_2CH_3$, which is generated as an intermediate or byproduct of the reaction with hydrogen, methane or other dehydrogenating agent. In accordance with such theory, the intermediate formula (IA) compound is then converted to the desired compound of formula (II), preferably HFO-1234yf, under the existing reaction conditions, and preferably on the surface of the catalyst.

In an alternative to the above reaction, the reducing agent comprises methane and the reaction is represented, without limitation, as follows:

$$CF_3CF_2CH_2Cl+CH_4 \rightarrow CF_3CF=CH_2+CH_3Cl+HF$$

In certain preferred embodiments, the stream containing the compound of formula (I), and preferably (IA) is preheated, primarily to avoid condensation, to a temperature of from about 50° C. to about 90° C., preferably about 60° C. to about 70° C., and introduced into a reaction vessel. The appropriate amount of the reducing agent, which is preferably from about 0.1% to about 500% of the stoichometric amount, is then added to the reaction vessel. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

Thus, it is contemplated that the dehydrohalogenation reaction step may be preformed using a wide variety of process parameters and process conditions in view of the overall teachings contained herein. However, it is preferred in certain embodiments that this reaction step comprise a gas phase reaction, preferably in the presence of catalyst, and even more preferably a carbon- and/or metal-based catalyst, such as activated carbon, palladium on carbon, palladium-based catalyst (including palladium on carbon and palladium on aluminum oxides), and ruthenium-based catalysts (including ruthenium on aluminum oxides). It is expected that many other catalysts may be used depending on the requirements of particular embodiments in view of the teachings contained herein. Of course, two or more any of these catalysts, or other catalysts not named here, may be used in combination.

In general it is preferred that the catalysts are fluorinated, preferably for a period of from about several hours (eg, 6 hours). In preferred embodiments, fluorination of the catalysts comprises exposing the catalyst to a stream of HF at about reaction temperature and under slight pressure, for example about 5-150 psia.

The gas phase dehydrohalogenation reaction may be conducted, for example, by introducing a gaseous form of a compound of formula (I), and preferably (IA) and a gaseous form of the reducing agent (and/or dehydrohalogenation agent), into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable reduction/dehydrohalogenation catalyst, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step, particularly where the formula (I) compound comprises (and even more preferably consists essentially of compounds of formula (1A)) is from about 400° C. to about 800° C., preferably about 400° C. to about 700° C. For such formula (1A) embodiments in which the reducing agent comprises, and even more preferably consists essentially of hydrogen, the reaction temperature for the dehydrohalogentation step is preferably from about 450° C. to about 600° C., more preferably about from 450° C. to about 550° C. For such formula (1A) embodiments in which the reducing agent comprises, and even more preferably consists essentially of methane, the reaction temperature for the dehydrohalogentation step is preferably from about 500° C. to about 700° C., more preferably from about 600° C. to about 700° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum, and in certain preferred embodiments is from about 15 to about 120 psia.

In certain embodiments, an inert diluent gas, such as nitrogen, may be used in combination with the other reactor feeds. When such a diluent is used, it is generally preferred that the compound of formula (I) comprise from about 5% to greater than 99% by weight based on the combined weight of diluent and formula (I) compound.

It is contemplated that the amount of catalyst use will vary depending on the particular parameters present in each embodiment. In certain preferred embodiments, the contact time is from about 0.1 seconds to about 1000 second, and preferably from about 2 seconds to about 50 seconds. For embodiments in which the compound of formula (I) comprises or consists essentially of a compound of formula (IA) and the reducing agent comprises or consists essentially of hydrogen, and particularly where the desired product of formula (II) is HFO-1234yf, applicants have found that it is preferred to use as the catalyst a carbon-based catalyst, such as activated carbon, or palladium-based catalyst, or a catalyst comprising palladium and carbon, such as a palladium on carbon catalyst.

For embodiments in which the compound of formula (I) comprises or consists essentially of a compound of formula (IA) and the reducing agent comprises or consists essentially of methane, and particularly where the desired product of formula (II) is HFO-1234yf, applicants have found that it is preferred to use as the catalyst a carbon-based catalyst, such as activated carbon, or a catalyst based on a Period 6 metal (particularly Cs and Ba) such as $BaNO_3$ or $CsNO_3$ (including in combination with aluminum-based catalyst or catalyst support, such as $Al_2O_3$), or Ni-based catalyst (such as Ni mesh) and combinations of these.

Preferably in such dehydrofluorination embodiments as described in this section, the conversion of the formula (I) compound is at least about 50%, more preferably at least about 65%, and even more preferably at least about 90%. Preferably, the selectivity to HFO-1234yf is at least about 70%, more preferably at least about 80% and more preferably at least about 90%.

B. Liquid Phase Reduction

One preferred reaction step in accordance may be described by those reactions in which the compound of formula (I) comprises a compound in which n is 1, that is a compound of formula (IB)

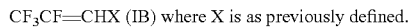

$CF_3CF=CHX$ (IB) where X is as previously defined.

For example, one preferred compound of formula (IB) is 3,3,3,2-tetrafluoro-1-chloro-1-propene ($CF_3CF=CHCl$).

It is contemplated that the reduction reaction step may be preformed using a wide variety of process parameters and process conditions in view of the overall teachings contained herein. However, it is preferred in certain embodiments that this reaction step comprise a liquid phase reaction, preferably in the presence of catalyst, and even more preferably in the presence of a catalyst contained in a liquid carrier, such as a solvent for at least one or more of the organic reactants.

Although it is contemplated that many solvents and catalysts will be adaptable for use in connection with these preferred embodiments, it is generally preferred that the solvent comprises tetrahydrofuran, dioxane and the like, and any combinations of solvents including these. In such preferred embodiments, the catalysts preferably include palladium-based catalyst. In certain preferred embodiments the palladium based catalyst comprises, and in certain embodiments consists essentially of tetrakis(triphenylphosphine)palladium (0), $[Pd(PPh_3)_4]$ and/or tris(dibenzlideneacetone)dipalladium (0), $Pd_2(dba)_3$ and combinations of these. In certain preferred embodiments, ligands for the catalyst are included in the reaction mixture, and although many ligands are believed to adaptable for use with the preferred catalyst systems of the present invention, in certain embodiments the ligands comprise tetraributyl phosphine, ammonium formate and combinations of these and/or other ligands. It is expected that other catalysts may be used depending on the requirements of particular embodiments in view of the teachings contained herein. Of course, two or more any of these catalysts, or other catalysts not named here, may be used in combination.

The liquid phase reduction reaction may be conducted, for example, by introducing the solvent and catalyst into a suitable reaction vessel or reactor. Preferably the vessel is comprised of materials which are resistant to corrosion as Hastelloy, Inconel, Monel and/or fluoropolymers linings.

Prior to its introduction to the reactor, the compound of formula (I), preferably including a compound of formula (IB), is preferably cooled to below its boiling point, and preferably to a temperature of from about −5° C. to about 20° C. and introduced into the solvent. The reaction mixture is then preferably brought to a temperature of from about −20° C. to about −50° C., and even more preferably to about −30° C. to about −40° C. and then a partial vacuum is applied to pull residual air or $O_2$ from the reactor. The reaction mixture is then preferably heated, preferably with agitation (such as stirring) to a temperature of from about 10° C. to about 200° C., more preferably from about 20° C. to about 150° C., and the reaction mixture is preferably maintained at this temperature for a time period of from about 1 hour to about 48 hours, more preferably from about 15 hours to about 30 hours. During this time period the pressure in the reactor may increase in certain embodiments to about 150 psig to about 250 psig, and even more preferably from about 150 psig to about 200 psig.

It is contemplated that the amount of catalyst use will vary depending on the particular parameters present in each embodiment. In certain preferred embodiments, the weight ratio of the compound of formula (I) to catalyst is from about 50,000:1 to about 1:1, and even more preferably from about 100:1 to about 1:1.

Preferably in such reduction embodiments as described in this section, the conversion of the formula (IB) compound is at least about 85%, more preferably at least about 95%, and even more preferably about 100%. Preferably, the selectivity to HFO-1234yf is at least about 20%, more preferably at least about 30% and more preferably at least about 40%.

EXAMPLES

Additional features of the present invention are provided in the following examples, which should not be construed as limiting the claims in any way.

Examples 1-11

These examples illustrate gas phase dehydrohalogenation of $CF_3CF_2CH_2Cl$ (HFC-235cb) to CF3CF=CH2 (1234yf).

A 22-inch (½-inch diameter) Monel tube reactor is charged with 120 cc of catalyst, as specified in Table 1 below. The reactor is mounted inside a heater with three zones (top, middle and bottom). The inlet of the reactor is connected to a pre-heater, which was kept at 300° C. by electrical heating. Organic (235cb) is fed from a cylinder kept at 65° C. A flow of reducing agent comprising hydrogen gas and the inert $N_2$ gas is maintained at a rate as indicated in Table 1 below. The reactor temperature is brought to the temperature indicated in the table. The HFC-235cb is passed through gas-flow controllers into a preheater maintained a temperature of about 300° C. The gas stream coming out of the preheater is passed through the catalyst bed at the desired temperature over a specified period of time and at a pressure of from about 2.5-5.3 psig. An on-line GC and a GCMS are used to analyze samples taken at the reactor exit line at regular time intervals. Finally, the reactor effluent is introduced into a 20-60% KOH scrubber solution, and the effluent from the scrubber solution is then condensed to collect the products. The desired product $CF_3CF = CH_2$ (1234yf) is then isolated from the mixture by distillation. The conversion of HFC-235cb is from about 50% to about 100% and the selectivity to HFO-1234yf is from about 60% to about 100%, depending on the reaction conditions. The major byproducts were $CF_3CF_2CH_3$ (HFC-245cb), $CF_3CF_2Cl$ (CFC-115), $CF_3Cl$ (CFC-13), and $CF_3CF = CHCl$.

The results are shown in Table 1 below.

TABLE 1

$CF_3CF_2CH_2Cl$ (HFC-235cb) + $H_2$ → $CF_3CF = CH_2$ (1234yf) + HCl + HF

| Example#/ Catalyst | T, °C. | H2/N2, Sccm | HFC-235cb, sccm | % Conv. of 235cb | % Selec. to 1234yf | % Selec. to 245cb | % Selec. to R* | % Selec. to R** |
|---|---|---|---|---|---|---|---|---|
| Example 1/A | 450 | 58/0 | 52 | 76 | 60 | 31 | 4 | 4 |
| Example 2/A | 500 | 61/0 | 54 | 100 | 90 | 9 | 0 | 1 |
| Example 3/A | 550 | 61/0 | 54 | 100 | 84 | 6 | 1 | 6 |
| Example 4/A | 600 | 63/0 | 57 | 97 | 63 | 12 | 0 | 24 |
| Example 5/B | 520 | 41/100 | 96 | 80 | 60 | 20 | 5 | 10 |
| Example 6/B | 550 | 41/100 | 138 | 58 | 36 | 40 | 7 | 16 |
| Example 7/C | 500 | 61/0 | 54 | 87 | 69 | 20 | 4 | 6 |
| Example 8/D | 500 | 61/0 | 54 | 80 | 63 | 26 | 3 | 7 |
| Example 9/E | 500 | 61/0 | 63 | 100 | 73 | 16 | 2 | 8 |
| Example 10/F | 500 | 61/0 | 76 | 91 | 30 | 27 | 10 | 30 |
| Example 11/G | 500 | 61/0 | 100 | 80 | 28 | 29 | 8 | 32 |

Catalysts (100 cc):
A is Calgon activated carbon
B is Shiro-Saga activated carbon;
C is Aldrich activated carbon;
D is NORIT RFC 3 activated carbon;
E is 0.5 wt % Pd/C;
F is 0.5 wt % Pd/Al2O3;
G is 0.5 wt % Ru/Al2O3
Byproducts:
R* is $CF_3CF = CHCl$ and
R** is combination of CF3Cl and CF3CF2Cl Examples 12-15

These examples illustrate gas phase hydrodehydrochlorination of $CF_3CF2CH_2Cl$ to $CF_3CF = CH_2$ (HFO-1234yf) using methane as the reducing agent. The protocol of Examples 1-11 is repeated except as indicated in Table 2 below.

TABLE 2

$CF_3CF_2CH_2Cl$ (235cb) + $CH_4$ → $CF_3CF = CH_2$ (1234yf) + $CH_3Cl$ + HF

| Example#/ Catalyst | T, °C. | P, psig | CH4, sccm | HFC-235cb, sccm | % Conv. of 235cb | % Selec. to 1234yf |
|---|---|---|---|---|---|---|
| Example 12/H | 560 | 10 | 50 | 50 | 17 | 0 |
| Example 13/I | 650 | 8 | 100 | 86 | 46 | 26 |
| Example 14/J | 650 | 7 | 97 | 83 | 52 | 31 |
| Example 14*/K | 650 and 500* | 8 | 96 | 87 | 54 | 40 |
| Example 15/L | 585 | 3 | 79 | 100 | 77 | 33 |

Catalysts (100 cc):
H is activated carbon
I 3 wt % BaNO3/Al2O3;
J is 3 wt % BaNO3/Al2O3 with 0.5 wt % CsNO3 used as a promoter,
K is a two zone reaction with two catalysts, specifically 50 cc CsNO3 promoted with BaNO3/Al2O3 is used at 650° C. in the first zone and 50 cc Calgon activated carbon is used at 500° C. in the second zone;
L is Ni mesh.
*two zone reaction Example 16

This example illustrates the liquid phase reduction of $CF_3CF = CHCl$ to $CF_3CF = CH_2$ (1234yf) with $Pd(PPh_3)_4$ catalyst. A 250 mL Parr reactor/autoclave is charged with 30 mL tetrahydrofuran to which 0.5 grams (0.04 mmol) [tetrakis (triphenylphosphine)palladium(0), [Pd(PPh3)4], 10.0 grams of ammonium formate (158 mmol), and 11.4 grams cold (0-10° C.) CF3CF = CHCl (77 mmol) are added under nitrogen. The reactor is sealed immediately, cooled to −30 to −40° C., and partially evacuated. The contents in the Parr reactor are brought to room temperature and gradually heated to 100° C. with stirring. The reactants are maintained at this temperature for 24 hours. During this time, the pressure in the reactor is increased to approximately 180-200 psig. The reactor is then cooled to 25° C. and the volatile materials are collected in an evacuated metal cylinder.

Gas chromatographic (GC) analysis of the volatile materials indicated $CF_3CF=CH_2$ as the main product with trace amounts of $CF_3CF=CHCl$ and carbon dioxide. The reaction mixture is cooled to 0° C. and filtrate is analyzed by gas chromatograph (GC) which indicates approximately a 40% conversion of $CF_3CF=CHCl$ to $CF3CF=CH_2$. Identity of $CF_3CF=CH_2$ is confirmed by comparison with a known sample. Purification of the product is accomplished by passing the product through a cold trap to remove $CO_2$ and unreacted starting material at about −70° C. and then distillation.

Example 17

This example illustrates the liquid phase reduction of $CF_3CF=CHCl$ to $CF_3CF=CH_2$ (HFO-1234yf) with $Pd_2(dba)_3$ catalyst. A 250 mL Parr reactor/autoclave was charged with 30 mL tetrahydrofuran (30 mL) to which 0.456 grams of tris(dibenzlideneacetone)dipalladium(0), $Pd_2(dba)_3$ (2.0 mmol), 0.8 grains of tributyl phosphine (2.0 mmol), 8.0 grams of ammonium formate (126 mmol), and 11.4 grams of cold (5-10° C.) $CF_3CF=CHCl$ (77 mmol) are added under nitrogen. The reactor is sealed immediately, cooled to the range of from about −30° C. to about −40° C., and partially evacuated. The contents in the Parr reactor are brought to room temperature and then gradually heated to 100° C. with stirring. The reactants are maintained at this temperature for 24 hours during which the internal pressure rises to approximately 200 psig. The reactor is then cooled to 25° C. and the volatile materials are passed through a trap at about −70° C. to about −78° C. and collected in a cold evacuated metal cylinder. Gas chromatographic (GC) analysis of the volatile materials collected indicate $CF_3CF=CH_2$ as the main product with trace amounts of $CF_3CF=CHCl$ and carbon dioxide. The reaction mixture was cooled to 0° C. and filtrate was analyzed by GC which indicated approximately a 35% conversion of $CF_3CF=CHCl$ to $CF_3CF=CH_2$.

Example 18

This example illustrates the liquid phase reduction of $CF_3CF=CHCl$ to $CF_3CF=CH_2$ (HFO-1234yf) with $Pd_2(dba)_3$ catalyst. Example 17 is repeated except that dioxane is substituted for tetrahydrafuran as the solvent. The result is essentially the same as Example 17.

Example 19

This example illustrates the liquid phase reduction of $CF_3CF=CHCl$ to $CF_3CF=CH2$ (HFO-1234yf) using $Pd_2(dba)_3 \cdot CHCl_3$ catalyst. The reaction is carried out as in Example 17 except that an equivalent amount of catalyst $Pd_2(dba)_3$ is substituted by tris(dibenzlideneacetone)dipalladium (0) chloroform complex, $Pd_2(dba)_3 \cdot CHCl_3$. The extent of conversion of $CF_3CF=CHCl$ to $CF_3CF=CH_2$ was essentially the same as in Example 17.

Example 20

This example illustrates the liquid phase reduction of $CF_3CF=CHCl$ to $CF_3CF=CH_2$ (HFO-1234yf) with $Pd(PPh_3)_4$ catalyst in tetrahydrofuran. A 250 mL Parr Reactor/autoclave was charged with 30 mL of tetrahydrofuran to which 0.5 grams of tetrakis(triphenylphosphine)palladium (0), $Pd(PPh_3)_4$ (0.04 mmol), 10 grams of ammonium formate (158 mmol), and 11.4 grams of $CF3CF=CHCl$ (61 mmol) were added under nitrogen. The reactor is sealed immediately, cooled to −30 to −40° C., and partially evacuated. The contents in the Parr reactor were brought to room temperature and gradually heated to 100° C. with constant stirring. The reactants are maintained at this temperature for 24 hours. The reactor was then cooled to 25° C. and the volatile materials were collected in an evacuated metal cylinder. Gas chromatographic (GC) analysis of the volatile materials indicated that $CF_3CF=CH_2$ and $CF_3CH=CHCl$ are present at a ratio of about 57:42. Carbon dioxide was also present. The reaction mixture was cooled to 0° C. and filtered under pressure, the filtrate was analyzed by GC which indicated about a 40% conversion of $CF_3CF=CHCl$ to $CF_3CH=CH_2$.

Examples 21-29

These examples illustrate gas phase dehydrohalogenation of $CF_3CF_2CH_3$ (HFC-245cb) to $CF_3CF=CH_2$ (HFO-1234yf). A 22-inch (½-inch diameter) Monel tube reactor is charged with 120 cc of catalyst, as specified in Table 1 below. The reactor is mounted inside a heater with three zones (top, middle and-bottom). The inlet of the reactor is connected to a pre-heater, which was kept at 300° C. by electrical heating. Organic (HFC-245cb) is fed from a cylinder kept at 65° C. A flow of reducing agent comprising hydrogen gas is maintained at a rate as indicated in Table 3 below. The reactor temperature is brought to the temperature indicated in the table. The HFC-245cb is passed through gas-flow controllers into a preheater maintained a temperature of about 300° C. The gas stream coming out of the preheater is passed through the catalyst bed at the desired temperature over a specified period of time and at a pressure of from about 2.5-5.3 psig. An on-line GC and a GCMS are used to analyze samples taken at the reactor exit line at regular time intervals. Finally, the reactor effluent is introduced into a 20-60% KOH scrubber solution, and the effluent from the scrubber solution is then condensed to collect the products. The desired product $CF_3CF=CH_2$ (HFO-1234yf) is then isolated from the mixture by distillation. The conversion of HFC-245cb is from about 30% to about 70% and the selectivity to HFO-1234yf is from about 90% to about 100%, depending on the reaction conditions.

The results are shown in Table 3 below.

TABLE 3

| $CF_3CF_2CH_3$ (HFC-245cb) → $CF_3CF=CH_2$ (1234yf) | | | | |
|---|---|---|---|---|
| Example#/ Catalyst | T, ° C. | H2/N2, sccm | HFC-245cb, sccm | % Conv. of 245cb | % Selec. to 1234yf |
| Example 21/M | 575 | 0 | 65 | 79 | 63 |
| Example 22/N | 575 | 0 | 68 | 82 | 57 |
| Example 23/O | 575 | 0 | 73 | 73 | 61 |
| Example 24/P | 575 | 0 | 68 | 84 | 59 |
| Example 25/P | 575 | 20 | 68 | 89 | 73 |
| Example 26/Q | 550 | 0 | 69 | 92 | 53 |
| Example 27/R | 550 | 0 | 67 | 93 | 33 |
| Example 28/S | 550 | 0 | 69 | 73 | 46 |

Catalysts (100 cc):
M is NORIT RFC 3;
N is Shiro-Saga activated carbon;
O is Aldrich activated carbon;
P is Calgon activated carbon;
Q is 0.5 wt % Pd/C;
R is 0.5 wt % PVC;
S is Ni-mesh

Example 29

This example illustrates the addition formation of compounds of formula (I) by the reaction of TFE with CH$_2$FCl in a gas phase reaction. Into a ½ inch flow reactor (Monel) 50 grams of freshly prepared catalyst (as indicated below) are charged. CF$_2$=CF$_2$ (TFE) and CH$_2$FCl (R31) are passed through a mass flow controller with a desired flow rate (as indicated below) to the preheater from respective cylinders connected with regulators. The preheater was connected to the reactor and always kept 10° C. below the reactor temperature. The reactor was uniformly heated to the desired temperature by an external heating element with an automatic control. The exit line from the reactor was connected to an on-line GC and GCMS for analysis. A 15 wt % KOH scrubber solution was used at 50° C. to neutralize acids coming out from the reactor. The gas stream coming out of the scrubber solution was then condensed in a cylinder under liquid N2 and then finally fractionated (distilled) to isolate products. SbF$_5$/C and AlCl$_3$/C are used as the catalyst. At 50° C. and under 30 psig reactor pressure, when 50 sccm of TFE and 150 sccm of R31 were passed over SbF5/C to achieve a 26% conversion of TFE and an 82% selectivity to CF$_3$CF$_2$CH$_2$Cl. When AlCl13/C is used as the catalyst, a 35% conversion and 78% selectivity to CF$_3$CF$_2$CH$_2$Cl was obtained.

Example 30

This example illustrates the addition formation of compounds of formula (I) by the reaction of CTFE with CH$_2$FCl in a gas phase reaction. Example 28 is repeated expect that CTFE is used in place of TFE. The major reaction products include CF$_3$CClFCH$_2$Cl and F$_2$ClCCF$_2$CH$_2$Cl at a 21% conversion (CTFE) level.

Example 31

This example illustrates the formation of compounds of formula (I) by the reaction of TFE with CH$_2$FCl in a gas phase reaction. Into a 300 ml autoclave, 0.1 mol C$_2$F$_4$ was reacted with 0.2 mol CH$_2$ClF in the presence of 0.05 mol of AlCl$_3$ at 20-30° for 3 hr to give 60% yield to CF$_3$CF$_2$CH$_2$Cl which was then isolated and purified by distillation.

Example 32

This example illustrates the formation of compounds of formula (I) by the reaction of TFE with CH$_2$FCl in a gas phase reaction. Into a 300 ml autoclave, 0.1 mol C$_2$F$_4$ was reacted with 0.2 mol CH$_2$ClF in the presence of 0.05 mol of AlCl$_3$ at 20-30° for 3 hr to give 60% yield to CF$_3$CF$_2$CH$_2$Cl which was then isolated and purified by distillation.

Example 33

This example illustrates the formation of compounds of formula (I) by the reaction of CTFE with CH$_2$FCl in a gas phase reaction. Into a 300 ml autoclave, 0.1 mol C F$_2$=CFCl was reacted with 0.2 mol CH$_2$ClF in the presence of 0.05 mol of AlCl$_3$ at 20-30° for 3 hr to give 60% yield to CF$_3$CClFCH$_2$Cl and F$_2$ClCF$_2$CH$_2$Cl which was then isolated and purified by distillation.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising
   (a) reacting at least one fluorinated C2 olefin with at least one addition agent under conditions effective to produce a compound of formula (I), $$CF_3CF_nCH_mX_{a-m} \qquad (I)$$

where each X is independently Cl, I or Br; n is 1 or 2; m is 1, 2 or 3, a is 2 or 3, and a-m $\geq$ 0, provided that when n is 1, m is 1 or 2 and provided that valence of each carbon atom is satisfied, wherein at least one fluorinated C2 olefin comprises a compound of formula III $$CY_2=CY_2 \qquad (III)$$

where each Y is independently F, Cl, I or Br, provided that there is at least one F on each carbon atom, and wherein at least one addition agent comprises a compound of formula (IV)

$$CH_mY_{a-m} \qquad (IV)$$

where m is 1, 2 or 3; a is 4, and a-m$\geq$0;
   (b) dehydrohalogenating the at least one compound of formula (I) to at least one compound of formula (II)

$$CF_3CZ=CHZ \qquad (II)$$

in the presence of hydrogen as a reducing agent that reduces at least one compound of formula (I) to at least one compound of formula (II), wherein each Z is independently H or F and where at least one compound of formula I is not the same as at least one compound of formula II.

2. The method of claim 1 wherein said compound of formula (III) comprises as compound of formula (IIIA) CF$_2$=CY$_2$ (IIIA) where each Y is independently F or Cl, and the compound of formula (IV) comprises a compound of formula CH$_2$FCl.

3. The method of claim 1 wherein said fluorinated C2 olefin comprises tetrafluoroethylene.

4. The method of claim 1 wherein said step of reacting a compound of formula (III) is carried out under conditions effective to convert at least about 15% of said compound of formula (III).

5. The method of claim 1 wherein said step of reacting a compound of formula (III) is carried out under conditions effective to provide selectivity to compound(s) of formula (I) of at least about 50%.

6. The method of claim 1 wherein said step of reacting a compound of formula (III) is carried out under conditions effective to provide a selectivity to compound(s) of formula (I) of at least about 70%.

7. The method of claim 1 wherein said dehydrohalogenating step is carried out under conditions effective to provide a formula (I) conversion of at least about 40%.

8. The method of claim 1 wherein said dehydrohalogenating step is carried out under conditions effective to provide a formula (I) conversion of at least about 90%.

9. The method of claim 6 wherein said dehydrohalogenating step is carried out under conditions effective to provide a formula (II) selectivity of at least about 40%.

10. The method of claim 1 wherein said dehydrohalogenating step is carried out under conditions effective to provide a formula (II) selectivity of at least about 90%.

11. The method of claim 1 wherein said reacting step comprises introducing said compounds of formulas (III) and (IV) to a reactor containing catalyst.

12. The method of claim 11 wherein said catalyst is selected from the group consisting of carbon, activated carbon, palladium, palladium on carbon, palladium on aluminum oxides, ruthenium, and ruthenium on aluminum oxides.

13. The method of claim 1 wherein at least one of said reacting step or said dehydrohalogenating step is a continuous process.

14. The method of claim 1, wherein the compound of formula (II) is 2,3,3,3-tetrafluoropropene.

15. The method of claim 1 wherein said dehydrohalogenating step is in a gas phase.

16. A method of preparing fluorinated organic compounds comprising dehydrohalogenating at least one compound of formula:

$$CF_3CF_2CH_3$$

to at least one compound of the following formula $$CF_3CZ=CH_2$$

in the presence of a reducing agent, where each Z is independently H or F.

17. A method of preparing fluorinated organic compounds comprising:
(a) reacting fluorinated C2 olefin with an addition agent under conditions effective to produce at least one compound of formula (I)
$CF_3CF_nCH_mX_{a-m}$ (I) wherein said compound of formula (I) is not $CF_3CF_2CH_3$;
(b) converting at least one compound of said formula I to $CF_3CF_2CH_3$ and
(c) dehydrohalogenating at least one of $CF_3CF_2CH_3$ to at least one compound of the following formula $$CF_3CZ=CH_2,$$

wherein steps (b) and (c) are in the presence of a reducing agent where each X is independently Cl, I or Br; each Z is independently H or F; n is 1 or 2; m is 1, 2 or 3, a is 2 or 3, and a-m $\geq$ 0, provided that when n is 1, m is 1 or 2 and provided that valence of each carbon atom is satisfied.

18. A method of preparing fluorinated organic compounds comprising dehydrohalogenating at least one compound of formula (I):

$$CF_3CF_nCH_mX_{a-m} \quad (I); \text{ and}$$

to at least one compound of formula (II)

$$CF_3CZ=CHZ \quad (II)$$

in the presence of hydrogen as a reducing agent that reduces at least one compound of formula (I) to at least one compound of formula (II), where each X is independently Cl, I or Br; each Z is independently H or F; n is 1 or 2; m is 1, 2 or 3, a is 2 or 3, and a-m $\geq$ 0, provided that when n is 1, m is 1 or 2 and provided that valence of each carbon atom is satisfied, and wherein said dehydrohalogenating step is carried out under conditions effective to provide a formula (II) selectivity of at least about 90%.

19. The method of claim 18 further comprising forming said compound of formula (I) by a method comprising reacting fluorinated C2 olefin with an addition agent under conditions effective to produce a compound of formula (I).

20. The method of claim 19 wherein said fluorinated C2 olefin comprises a compound of formula (III) $CY_2=CY_2$
where each Y is independently F, Cl, I or Br, provided that there is at least one F on each carbon atom, and wherein said addition agent is a compound of formula (IV)

$$CH_mY_{a-m} \quad (IV)$$

where m is 1, 2 or 3; a is 4, and a-m $\geq$ 0.

21. The method of claim 20 wherein said compound of formula (III) comprises as compound of formula (IIIA) $CF_2=CY_2$ (IIIA) where each Y is independently F or Cl, and the compound of formula (IV) comprises a compound of formula $CH_2FCl$.

22. The method of claim 20 wherein said fluorinated C2 olefin comprises tetrafluoroethylene.

23. The method of claim 18 wherein at least one of said reacting step or said dehydrohalogenating step is a continuous process.

24. The method of claim 18, wherein the compound of formula (II) is 2,3,3,3-tetrafluoropropene.

* * * * *